United States Patent [19]
Sachs et al.

[11] Patent Number: 6,132,768
[45] Date of Patent: Oct. 17, 2000

[54] ORAL PHARMACEUTICAL COMPOSITION WITH DELAYED RELEASE OF ACTIVE INGREDIENT FOR REVERSIBLE PROTON PUMP INHIBITORS

[75] Inventors: George Sachs, Encino, Calif.; Rango Dietrich, Constance, Germany

[73] Assignee: BYK Gulden Lomberg Chemische Fabrik GmbH, Constance, Germany

[21] Appl. No.: 08/498,391

[22] Filed: Jul. 5, 1995

[51] Int. Cl.$^7$ ................................ A61K 9/22; A61K 9/54
[52] U.S. Cl. .................... 424/458; 424/457; 424/468; 424/472; 424/474; 424/489; 424/490
[58] Field of Search ..................... 424/464, 489, 424/490, 457, 472, 474, 468, 458

[56] References Cited

U.S. PATENT DOCUMENTS

| | | | |
|---|---|---|---|
| 3,456,049 | 7/1969 | Hotko et al. | 424/22 |
| 4,464,372 | 8/1984 | Bristol et al. | 424/250 |
| 4,692,337 | 9/1987 | Ukigaya et al. | 424/469 |
| 4,994,276 | 2/1991 | Baichwal et al. | 424/440 |
| 5,041,442 | 8/1991 | Romero et al. | 514/249 |
| 5,409,903 | 4/1995 | Polak et al. | 514/23 |
| 5,476,669 | 12/1995 | Borody | 424/653 |
| 5,599,794 | 2/1997 | Eek et al. | 514/29 |

*Primary Examiner*—James M. Spear
*Attorney, Agent, or Firm*—Jacobson, Price, Holman & Stern, PLLC

[57] ABSTRACT

An oral pharmaceutical composition of a reversible proton pump inhibitor in pellet or tablet form, wherein the reversible proton pump inhibitor is at least partly in slow-release form, is distinguished, on combined administration with an antimicrobially-active ingredient, by an enhanced action of rapid onset against disorders caused by Helicobacter.

18 Claims, No Drawings

ORAL PHARMACEUTICAL COMPOSITION WITH DELAYED RELEASE OF ACTIVE INGREDIENT FOR REVERSIBLE PROTON PUMP INHIBITORS

RELATED APPLICATION

This application is related to Applicants' concurrently-filed application U.S. Ser. No. 08/498,386 filed Jul. 5, 1995, now U.S. Pat. No. 5,945,124.

FIELD OF THE INVENTION

The present invention relates to oral pharmaceutical compositions in pellet or tablet form for reversible proton pump inhibitors for combined use with antimicrobially-active ingredients for the treatment of disorders caused by Helicobacter.

PRIOR ART

Control of the microbe *Helicobacter pylori*, which is thought to be responsible for certain gastric disorders, by combined use of an antimicrobially-active ingredient which is active against *Helicobacter pylori* and of an agent which reduces gastric acid has been regarded as the method of choice for some time.

Besides inhibitors of gastric acid secretion of the $H_2$ receptor antagonist type, in recent times use has been made, with more or less success, of compounds of the class of so-called irreversible proton pump inhibitors (such as pantoprazole, omeprazole or lansoprazole). Irreversible proton pump inhibitors are substances which covalently, and thus irreversibly, bind to the enzyme which is responsible for acid secretion in the stomach, the $H^+/K^+$ ATPase.

Besides so-called irreversible proton pump inhibitors, which essentially have a common basic chemical structure (pyridinylmethylsulfinylbenzimidazoles), there are the so-called reversible $H^+/K^+$ ATPase inhibitors which have different basic chemical structures and which, as the name indicates, reversibly bind to the enzyme responsible for gastric acid secretion. These are called reversible proton pump inhibitors in connection with the present invention. Reversible proton pump inhibitors are disclosed, for example, in the documents JP-A-3031280, DE-A-3917232, EP-A-0399267, EP-A-0387821, JP-A-3031280, JP-A-2270873, EP-A-0308917, EP-A-0268989, EP-A-0228006, EP-A-0204285, EP-A-0165545, EP-A-0125756, EP-A-0120589, EP-A-0509974, DE-A-3622036, EP-A-0537532, EP-A-0535529, JP-A-3284686, JP-A-3284622, U.S. Pat. No. 4,833,149, EP-A-0261912, WO-A-9114677, WO-A-9315055, WO-A-9315071, WO-A-9315056, WO-A-9312090, WO-A-9212969, WO-A-9118887, EP-A-0393926, EP-A-0307078, U.S. Pat. No. 5,041,442, EP-A-0266890, WO-A-9414795, EP-A-0264883, EP-A-0033094, EP-A-0259174, EP-A-0330485, WO-A-8900570, EP-A-0368158, WO-A-9117164, WO-A-9206979, WO-A-9312090, WO-A-9308190, WO-A-9418199, DE-A-3011490, U.S. Pat. No. 4,464,372, EP-A-0068378 and WO-A-9424130.

Combined use of reversible proton pump inhibitors with antimicrobially-active ingredients has a good effect against Helicobacter in vitro. However, the clinical effect achieved with this combined use is disappointing.

SUMMARY OF THE INVENTION

The action of an antimicrobially-active ingredient on Helicobacter is surprisingly enhanced by administering a reversible proton pump inhibitor in slow-release dosage form (extended release form). It must be regarded as particularly surprising that, in addition, administration of the slow-release reversible proton pump inhibitor results in the onset of action taking place significantly faster than on administration of a non-slow-release reversible proton pump inhibitor. The duration of treatment until Helicobacter is eradicated is shortened, saving considerable amounts of antibiotic and acid inhibitor.

The invention thus relates to oral pharmaceutical compositions in pellet or tablet form for reversible proton pump inhibitors for combined use with antimicrobially-active ingredients for the treatment of disorders caused by Helicobacter, wherein the reversible proton pump inhibitor is present at least partly in slow-release form.

DETAILS

Reversible proton pump inhibitors are, for the purpose of the present invention, those active ingredients which reversibly bind to the enzyme responsible for gastric acid secretion, $H^+/K^+$ ATPase. Examples of reversible proton pump inhibitors are enumerated in the previously-noted documents. Examples of reversible proton pump inhibitors are, e.g., 8-(2-methoxycarbonylamino-6-methylbenzylamino)-2,3-dimethylimidazo[1,2-a]pyridine (hereinafter B9401-011), 3-hydroxymethyl-8-(2-methoxycarbonylamino-6-methylbenzyloxy)-2 methylimidazo[1,2-a]pyridine, 3-hydroxymethyl-8-(2-methoxycarbonylamino-6-methylbenzyloxy)-2-methylimidazo[1,2-a]pyridine, 8-(2-methoxycarbonylamino-6-methylbenzyloxy)-2,3-dimethylimidazo[1,2-a]pyridine, 8-(2-tert-butoxycarbonylamino-6-methylbenzylamino)-2,3-dimethylimidazo[1,2-a]pyridine, 8-(2-tert-butoxycarbonylamino-6-methylbenzyloxy)-2,3-dimethylimidazo[1,2-a]pyridine, 8-(2-ethoxycarbonylamino-6-methylbenzylamino)-2,3-dimethylimidazo[1,2-a]pyridine, 8-(2-isobutoxycarbonylamino-6-methylbenzylamino)-2,3-dimethylimidazo[1,2-a]pyridine, 8-(2-isopropoxycarbonylamino-6-methylbenzylamino)-2,3-dimethylimidazo[1,2-a]pyridine, 8-(2-tert-butoxycarbonylamino-6-methylbenzylamino)-3-hydroxymethyl-2-methylimidazo[1,2-a]pyridine, 8-(2-tert-butoxycarbonylamino-6-methylbenzyloxy)-3-hydroxymethyl-2-methylimidazo[1,2-a]pyridine, 8-{2-[(2-methoxyethoxy)carbonylamino]-6-methylbenzyloxy}-2-methylimidazo[1,2-a]pyridine-3-methanol, 8-{2-[(2-methoxyethoxy)carbonylamino]-6-methylbenzylamino}-2-methylimidazo[1,2-a]pyridine-3-methanol, 8-{2-[(2-methoxyethoxy)carbonylamino]-6-methylbenzylamino}-2,3-dimethylimidazo[1,2-a]pyridine, 8-{2-[(2-methoxyethoxy)-carbonylamino]-6-methylbenzyloxy}-2-methylimidazo[1,2-a]pyridine-3-methanol, 8-{2-[(2-methoxyethoxy) carbonylamino]-6-methylbenzyloxy}-2,3-dimethylimidazo[1,2-a]pyridine, 3-hydroxymethyl-2-methyl-8-benzyloxyimidazo-[1,2-a]pyridine, 3-hydroxymethyl-2-trifluoromethyl-8-benzyloxyimidazo-[1,2-a]pyridine, 1,2-dimethyl-3-cyanomethyl-8-benzyloxyimidazo[1,2-a]pyridine, 2-methyl-3-cyanomethyl-8-benzyloxyimidazo[1,2-a]pyridine, 3-butyryl-8-methoxy-4-(2-methylphenylamino)quinoline and 3-butyryl-8-hydroxyethoxy-4-(2-methylphenylamino)quinoline.

Reversible proton pump inhibitors can, in this connection, be present as such, in the form of their salts and/or their solvates (e.g. hydrates), etc. Particularly suitable salts are (because all reversible proton pump inhibitors are substances with a basic reaction) all acid-addition salts. Particular mention may be made of the pharmacologically-acceptable salts of inorganic and organic acids customarily used in pharmaceutical technology, including water-soluble and water-insoluble acid-addition salts with acids, such as hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid and 3-hydroxy-2-naphthoic acid, the acids being used in the preparation of the salt in a ratio of amounts which are equimolar or different therefrom—depending on whether the acid is mono- or polybasic and depending on the salt required.

Examples of suitable antimicrobially-active ingredients (active against Helicobacter pylori) are enumerated in European Patent Application EP-A-282131. These active ingredients include, for example, bismuth salts (such as bismuth subcitrate or bismuth subsalicylate), sulfonamides, nitrofurans (such as nitrofurazone, nitrofurantoin or furazolidone), metronidazole, tinidazole, nimorazole or antibiotics. Examples of antibiotics which may be mentioned in this connection are, arranged according to particular classes of active ingredient: aminoglycosides, such as gentamicin, neomycin, kanamycin, amikacin or streptomycin; macrolides, such as erythromycin, azithromycin, clarithromycin, clindamycin or rifampicin; penicillins, such as penicillin G, penicillin V, ampicillin, mezlocillin or amoxicillin; polypeptides, such as bacitracin or polymyxin; tetracyclines, such as tetracyline, chlorotetracycline, oxytetracycline, minocycline or doxycycline; carbapenems, such as imipenem, loracarbef, meropenem or panipenem; cephalosporins, such as cefalexin, cefoxitin, cefuroxime axetil, cefotaxime, cefpodoxime proxetil, cefaclor, cefadroxil or cephalothin; gyrase inhibitors, such as ciprofloxacin, norfloxacin, ofloxacin or pefloxacin; or other different antibiotics, such as chloramphenicol. Particularly worthy of mention in this connection is also the combination of a plurality of antimicrobially-active ingredients, for example the combination of a bismuth salt and/or tetracycline with metronidazole, or the combination of amoxicillin or clarithromycin with metronidazole.

Particularly worthy of mention in this connection is also administration of a reversible proton pump inhibitor together with a plurality of antimicrobially-active ingredients, for example with the combination of a bismuth salt and/or tetracycline with metronidazole, or with the combination of amoxicillin or clarithromycin or with metronidazole.

The dosage of the active ingredients depends greatly on the nature of the reversible proton pump inhibitor used and of the antimicrobially-active ingredient(s) used. A typical dosage of a reversible proton pump inhibitor as disclosed, for example, in WO-A-9418199 can be regarded as a daily dose of from about 0.01 to about 20, preferably from 0.05 to 5, and in particular from 0.1 to 1.5, mg/kg of body weight, where appropriate in the form of a plurality of single doses. Penicillins, such as amoxicillin, are administered in a daily dose of from about 5 to 40, preferably from 10 to 20, mg/kg of body weight.

Antimicrobially-active ingredients which may be emphasized are erythromycin, azithromycin, clarithromycin, clindamycin, rifampicin, ampicillin, mezlocillin, amoxicillin, tetracycline, minocycline, doxycycline, imipenem, meropenem, cefalexin, cefuroxime axetil, cefpodoxime proxetil, cefaclor, cefadroxil, ciprofloxacin, norfloxacin, of loxacin and pefloxacin.

Clarithromycin and amoxicillin may be mentioned as antimicrobially-active ingredients which should be particularly emphasized.

Combined administration means (for the purpose of the present invention) fixed and, in particular, free combinations, i.e. the slow-release reversible proton pump inhibitor and the antimicrobially-active ingredient are present together in one dosage unit, or slow-release reversible proton pump inhibitor and antimicrobially-active ingredient, which are present in separate dosage units, are administered in direct succession or at a relatively large time interval; a relatively large time interval means within a time span of up to a maximum of 24 hours. For use as separate dosage units, these are preferably made available together in one pack. For example, the two dosage units are packed together in blister packs which are designed with regard to the relative arrangement of the two dosage units with respect to one another, the inscription and/or coloring in a manner known per se so that the times for taking the individual components (dosage regimen) of the two dosage units are evident to a patient.

A dosage unit means, in particular, those medicinal dosage forms in which slowing or extending of reversible proton pump inhibitor release is achieved with as few problems as possible. These include, in particular, tablets, coated tablets or pellets, and microtablets in capsules, with the dosage form advantageously being designed so that the two active ingredient components (reversible proton pump inhibitor on the one hand and antimicrobially-active ingredient on the other hand) are released, or made available effectively for the body, in such a way that an optimal active-ingredient profile (and thus action profile) is achieved.

For slowing release, various types and degrees of retarding release may be used to ensure a reversible proton pump inhibitor plasma level which persists as long as possible and is sufficient for raising pH.

The pharmaceutical formulation of the antimicrobially-active ingredient(s) is carried out in a manner which is familiar per se to the skilled worker for the individual active ingredients.

The rapid release of part of the reversible proton pump inhibitor and retarding release of another part is optionally achieved, for example, by layered tablets or multilayer tablets, in which part of the reversible proton pump inhibitor is present in an outer coating in a form without slowing release; this is followed by another coating containing the antimicrobially-active ingredient and then the core with the reversible proton pump inhibitor whose release is slowed in a suitable manner.

The details of how to achieve slowing release are familiar to the skilled worker on the basis of his expert knowledge. The skilled worker is likewise familiar with suitable ancillary substances and vehicles for the required dosage forms (pharmaceutical formulations). Besides solvents, tablet ancillary substances and other active ingredient excipients it is possible to use, for example, tablet-coating compositions, plasticizers, antioxidants, preservatives, dyes, etc. Where incompatibilities between the active ingredients or between the active ingredients and ancillary substances are to be expected, suitable separating layers must be provided where appropriate.

The oral pharmaceutical compositions according to the invention are distinguished from the prior art by controlled release of active ingredients and increased stability.

Besides filler and binder, other ancillary substances, in particular lubricants and nonstick agents, and tablet disintegrants, are used in the manufacture of the tablet cores. A suitable binder is, in particular, polyvinylpyrrolidone in various degrees of polymerization. Examples of lubricants and nonstick agents are higher fatty acids and their alkali-metal and alkaline-earth-metal salts, such as calcium stearate. Suitable tablet disintegrants are, in particular, chemically-inert agents. Preferred tablet disintegrants include cross-linked polyvinylpyrrolidone, crosslinked sodium carboxymethylcelluloses and sodium starch glycolate.

Examples of suitable film polymers, in respect of the water-insoluble release-slowing intermediate layer(s) to be applied to the pellet or tablet core, include ethylcellulose, polyvinyl acetate, Eudragit® RS, Eudragit® RL, etc. The release rate can be controlled not only by incorporating suitable water-soluble pore formers, such as PEG, lactose, mannitol, sorbitol, HPMC, etc., but also by the thickness of the coating layer applied.

The solvents or dispersants used for the release-controlling polymer dispersion are non-aqueous organic solvents, such as alcohols, ketones, halogenated hydrocarbons or mixtures of such solvents.

It is possible in a similar way to use osmotic systems with semipermeable membranes of cellulose acetate, cellulose acetate butyrate or cellulose acetate propionate (as described in U.S. Pat. No. 3,845,770, U.S. Pat. No. 3,916,899, U.S. Pat. No. 4,036,227, U.S. Pat. No. 4,093,708, U.S. Pat. No. 4,096,238, U.S. Pat. No. 4,135,514 and U.S. Pat. No. 4,142,526) to control the release of active ingredients. These can be coated with aqueous dispersions of enteric lacquers without changing the release rate.

Examples of suitable polymers for the enteric coating are methacrylic acid/methyl methacrylate copolymer or methacrylic acid/ethyl methacrylate copolymer (Eudragit® L) or cellulose derivatives, such as carboxymethylethylcellulose (CMEC, Duodcel), cellulose acetate phthalate (CAP), cellulose acetate trimellitate (CAT), hydroxypropylmethylcellulose phthalate (HP50, HP55), hydroxypropylmethylcellulose acetate succinate (HPMCAS) or polyvinyl acetate phthalate, to which it is also possible to add, if desired, plasticizer (such as propylene glycol) and/or other additives and ancillary substances (e.g. buffer base, such as, preferably, aluminum hydroxide; or pigment). The layers are applied in conventional ways using equipment customary for these purposes.

SUSCEPTIBILITY OF COMMERCIAL APPLICATION

The combined use according to the invention of a slow-release reversible proton pump inhibitor with an antimicrobially-active ingredient meets all the requirements for a pharmaceutical product or combination pharmaceutical product for the treatment of gastric disorders attributable to the microbe, *Helicobacter pylori*. The particular advantages connected with the combined use of the slow-release drug form with an antimicrobially-active ingredient which may be mentioned are: the rapid onset of action with pH values as far as neutral in the lumen of the stomach and in the wall of the stomach and an optimal displaying of the effect of the antimicrobially-active ingredient. The short duration of treatment which can be achieved increases the compliance, which is extremely important for antibiotic treatments.

EXAMPLES

The following formulation examples explain the invention in detail without restricting it.

Example 1

Tablets:

I. Production of Uncoated Core:

| a) | B9401-011 (hemimalate) | 119.8 mg |
|----|------------------------|----------|
| b) | Sodium carboxymethylstarch | 21.0 mg |
| c) | Microcrystalline cellulose (e.g.: Avicel PH 101 | 21.0 mg |
| d) | Maize starch | 19.4 mg |
| e) | Magnesium stearate | 5.0 mg |
|    |                      | 186.2 mg | a) is mixed with b), c) and part of d). A paste is prepared with the remainder of d). The latter is used for granulation of the powder mixture in a suitable mixer. The granules are dried in a drying oven or fluidized bed. e) is added to the dried granules, and the granules are compressed in a suitable tabletting machine.

II. Release-slowing Layer

| f) | Ethylcellulose | 9.85 mg |
|----|----------------|---------|
| g) | Lactose micronized | 2.37 mg |
| h) | Propylene glycol | 0.98 mg |
|    |                  | 14.00 mg | f) is dissolved in 165 ml of isopropanol. h) is stirred in for a sufficient length of time using a suitable agitator to form a solution (A). g) is suspended in 165 ml of isopropanol using a rotor-stator agitator to form a fine suspension (B). (A) and (B) are combined.

The tablet cores obtained under I are coated to an adequate layer thickness with the suspension obtained above in suitable apparatus.

Example 2

Tablets:

I. Production of Uncoated Core:

Production of the cores takes place as in Example 1, I.

II. Release-slowing Layer:

| f) | Polyvinyl acetate | 10.38 mg |
|----|-------------------|----------|
| g) | Lactose micronized | 2.59 mg |
| h) | Propylene glycol | 1.03 mg |
|    |                  | 13.13 mg | f) is dissolved in 150 ml of a 1:1 acetone/chloroform mixture. h) is stirred in for a sufficient length of time, using a suitable agitator to prepare a solution (A).

g) is suspended in 150 ml of a 1:1 acetone/chloroform mixture, using rotor-stator agitator to prepare a fine dispersion (B). (A) and (B) are combined.

The tablet cores obtained under I are coated to a sufficient layer thickness with the thus-obtained dispersion in suitable apparatus.

Example 3

Pellets:

I. Starter Pellets

| | | |
|---|---|---|
| a) | Sucrose pellets (0.7–0.85 mm) | 950.0 g |
| b) | Hydroxypropylmethylcellulose 2910 (USP) | 40.0 g |
| c) | Propylene glycol | 10.0 g | a) is sprayed with an aqueous solution of b) and c) in a fluidized bed (Wurster method).

II. Active Pellets

| | | |
|---|---|---|
| d) | B9401-011 (Hemimalate) | 403.0 g |
| e) | Hydroxypropylmethylcellulose 2910 (USP) | 403.0 g |
| f) | Propylene glycol | 201.5 g | d), e), f) are successively dissolved in 4 liters of purified water and sprayed onto 900 g of the pellets obtained under I in a fluidized bed (Wurster method).

III. Slow-release Pellets

A release-slowing layer is applied in analogy to the procedure described for tablets in a pan or fluidized bed.

Example 4

Pellets:

I. Active Pellets

| | | |
|---|---|---|
| a) | B9401-011 (Hemimalate) | 403.0 g |
| b) | Microcrystalline cellulose (Avicel PH101) | 117.0 g |
| c) | Na carboxymethylcellulose | 18.0 g | a) and b) are premixed dry and subsequently moistened to a paste-like consistency with a solution of Na carboxymethylcellulose in water in a conventional kneader or high-speed mixer. The resulting composition is then extruded and shaped into pellets by the extruder/rounder method familiar to the skilled worker. The moistened pellets are dried in suitable equipment (drying oven, fluidized bed, etc.).

III. Slow-release Pellets:

The release-slowing layer is applied in analogy to the procedure described for tablets in a pan or fluidized bed.

The invention and its advantages are readily understood from the foregoing description. As is apparent, various changes can be made in the products and methods without departing from the spirit and scope of the invention or sacrificing its material advantages. The products and processes hereinbefore described are merely illustrative of preferred embodiments of the invention.

What is claimed is:

1. An oral pharmaceutical reversible-proton-pump-inhibitor composition comprising a reversible-proton-pump inhibitor in combination with an antimicrobially-active ingredient for treating a disorder caused by Helicobacter, wherein at least part of the reversible-proton-pump inhibitor is in slow-release form, the composition including an effective amount of polymer to control release of at least part of the reversible-proton-pump inhibitor, whereby onset of action of the antimicrobially-active ingredient takes place significantly faster than on administration thereof with a non-slow-release reversible-proton-pump inhibitor.

2. An oral pharmaceutical composition as claimed in claim 1, wherein the reversible proton pump inhibitor, which is wholly or partly in controlled-release form, is in fixed combination with the antimicrobially-active ingredient in a single dosage unit.

3. An oral pharmaceutical composition as claimed in claim 2, wherein the reversible proton pump inhibitor is in pellet form together with the antimicrobially-active ingredient in a capsule as a dosage unit.

4. An oral pharmaceutical reversible-proton-pump-inhibitor composition comprising a reversible-proton-pump inhibitor in combination with an antimicrobially-active ingredient for treating a disorder caused by Helicobacter and wherein at least part of the reversible-pump-inhibitor is in slow-release form, the reversible-proton-pump inhibitor being together with the antimicrobially-active ingredient in a multilayer tablet.

5. A single package comprising an oral pharmaceutical composition as claimed in claim 1, wherein the reversible proton pump inhibitor and the antimicrobially-active ingredient are in separate dosage units.

6. A single package as claimed in claim 5, wherein the single package is a blister pack which is designed by the relative arrangement of individual components of the dosage units, by inscription and/or by coloring to communicate a dosage regimen to a patient.

7. An oral pharmaceutical reversible-proton-pump-inhibitor composition comprising a reversible-proton-pump inhibitor in combination with an antimicrobially-active ingredient for treating a disorder caused by Helicobacter and wherein at least part of the reversible-proton-pump inhibitor is in slow-release form, the reversible-proton-pump inhibitor being a member selected from group consisting of 8-(2-methoxycarbonylamino-6-methylbenzylamino)-2,3-di-methylimidazo[1,2-a]pyridine, 3-hydroxymethyl-8-(2-methoxycarbonylamino-6-methylbenzylamino)-2-methylimidazo[1,2-a]pyridine, 3-hydroxymethyl-8-(2-methoxycarbonylamino-6-methylbenzyloxy)-2-methylimidazo[1,2-a]pyridine, 8-(2-methoxycarbonylamino-6-methylbenzyloxy)-2,3-di-methylimidazo[1,2-a]pyridine, 8-(2-tert-butoxycarbonylamino-6-methylbenzylamino)-2,3-dimethylimidazo[1,2-a]pyridine, 8-(2-tert-butoxycarbonylamino-6-methylbenzyloxy)-2,3-dimethylimidazo[1,2-a]pyridine, 8-(2-ethoxycarbonylamino-6-methylbenzylamino)-2,3-dimethylimidazo[1,2-a]pyridine, 8-(2-isobutoxycarbonylamino-6-methylbenzylamino)-2,3-dimethylimidazo[1,2-a]pyridine, 8-(2-isopropoxycarbonylamino-6-methylbenzylamino)-2,3-dimethylimidazo[1,2-a]pyridine, 8-(2-tert-butoxycarbonylamino-6-methylbenzylamino)-3-hydroxymethyl-2-methylimidazo[1,2-a]pyridine, 8-(2-tert-butoxycarbonylamino-6-methylbenzyloxy)-3-hydroxymethyl-2-methylimidazo[1,2-a]pyridine, 8-{2-[(2-methoxyethoxy)carbonylamino]-6-methylbenzyloxy}-2-methylimidazo[1,2-a]pyridine-3-methanol, 8-{2-[(2-methoxyethoxy)carbonylamino]-6-methylbenzylamino}-2-methylimidazo[1,2-a]pyridine-3-methanol, 8-{2-[(2-methoxyethoxy)carbonylamino]-6-methylbenzylamino}-2,3-dimethylimidazo[1,2-a]pyridine, 8-{2-[(2-methoxyethoxy)carbonylamino]-6-methylbenzyloxy}-2-methylimidazo[1,2-a]pyridine-3-methanol, 8-{2-[(2-methoxyethoxy)carbonylamino]-6-methylbenzyloxy}-2,3-dimethylimidazo[1,2-a]pyridine, 3-hydroxylmethyl-2-methyl-8-benzyoxylimidazo[1,2-a]pyridine, 3-hydroxylmethyl-2-triflouromethyl-8-benzyloxyimidazo[1,2-a]pyridine, 1,2-dimethyl-3-cyanomethyl-8-benzyloxyimidazo[1,2-a]pyridine, 2-methyl-3-cyanomethyl-8-benzyloxyimidazo[1,2-a]pyridine, 3-butyryl-8-methoxy-4-(2-methylphenylamino)quinoline and 3-butyryl-8-hydroxyethoxy-4-(2-methylphenylamino)quinoline, or a salt thereof.

8. An oral pharmaceutical reversible-proton-pump-inhibitor composition comprising a reversible-proton-pump inhibitor in combination with an antimicbially-active ingredient for treating a disorder caused by Heliobacter and wherein part of the reversible-proton-pump inhibitor is in slow-release form, the reversible-proton-pump inhibitor being 8-(2-methoxycarbonylamino-6-methylbenzylamino)-2,3-di-methylimidazo[1,2-a]pyridine, or a salt thereof.

9. A pharmaceutical composition as claimed in claim 1, wherein the antimicrobially-active ingredient is a member selected from the group consisting of bismuth subcitrate, bismuth subsalicylate, nitrofurazone, nitrofurantoin, furazolidone, metronidazole, tinidazole, nimorazole, gentamicin, neomycin, kanamycin, amikacin, streptomycin, erythromycin, azithromycin, clarithromycin, clindamycin, rifampicin, penicillin G, penicillin V, ampicillin, mezlocillin, amoxicillin, bacitracin, polymyxin, tetracycline, chlorotetracycline, oxytetracycline, minocycline, doxycycline, imipenem, loracarbef, meropenem, panipenem, cefalexin, cefoxitin, cefuroxime axetil, cefotaxime, cefpodoxime proxetil, cefaclor, cefadroxil, cephalothin, ciprofloxacin, norfloxacin, ofloxacin, pefloxacin and chloramphenicol.

10. A process for the production of an oral pharmaceutical composition in pellet or tablet form for a reversible proton pump inhibitor, as active ingredient, or for combined use thereof with an antimicrobially-active ingredient for treating a disorder caused by Helicobacter, which comprises a) incorporating the active ingredient into a pellet or tablet core, b) applying thereto at least one release-slowing intermediate layer comprising a water-insoluble, release-slowing acidic film former and c) subsequently applying an outer enteric layer which is soluble in the small intestine.

11. A process as claimed in claim 10, wherein the water-insoluble, release-slowing film former for the intermediate layer is applied dissolved or dispersed in a solvent.

12. In a method for treating a disorder caused by Helicobacter with a reversible proton pump inhibitor, the improvement which comprises orally administering the reversible proton pump inhibitor in controlled-release form and also orally administering an antimicrobially-active ingredient to one afflicted with the disorder, whereby the reversible pump inhibitor in slow-release form enhances action of the antimicrobially-active ingredient on Helicobater.

13. A method of claim 12 wherein the reversible proton pump inhibitor and the antimicrobially-active ingredient are administered in direct succession.

14. A method of claim 12 wherein the reversible proton pump inhibitor and the antimicrobially-active ingredient are administered within a time span of up to 24 hours.

15. An oral pharmaceutical reversible-proton-pump-inhibitor composition of claim 1 in pellet or tablet form.

16. A process as claimed in claim 11, wherein the solvent is a non-aqueous organic solvent.

17. An oral pharmaceutical composition as claimed in claim 15, comprising at least one layer controlling release of active ingredient and formed from a water-insoluble, releae-slowing film former.

18. A method of claim 12 wherein the reversible proton pump inhibitor is in controlled-release form.

* * * * *